United States Patent
Draenert et al.

[11] Patent Number: 6,080,801
[45] Date of Patent: Jun. 27, 2000

[54] MULTI-COMPONENT MATERIAL AND PROCESS FOR ITS PREPARATION

[75] Inventors: Klaus Draenert, München; Helmut Wahlig, Darmstadt, both of Germany

[73] Assignee: Klaus Draenert, Munich, Germany

[21] Appl. No.: 09/115,323

[22] Filed: Jul. 14, 1998

Related U.S. Application Data

[62] Continuation of application No. 08/650,047, May 16, 1996, abandoned, which is a continuation of application No. 08/030,045, filed as application No. PCT/EP91/01746, Sep. 13, 1991.

[30] Foreign Application Priority Data

Sep. 13, 1990 [DE] Germany ............................... 40 29 136
Sep. 19, 1990 [DE] Germany ............................... 40 29 714

[51] Int. Cl.[7] ............................... A61L 27/16; A61F 2/00
[52] U.S. Cl. ........................ 523/115; 523/116; 523/117; 523/200; 523/205; 524/533; 524/560
[58] Field of Search .................................. 523/115, 116, 523/117, 200, 205; 524/533, 560

[56] References Cited

U.S. PATENT DOCUMENTS

| | | | |
|---|---|---|---|
| 3,789,029 | 1/1974 | Hodosh | 523/114 |
| 4,093,576 | 6/1978 | de Wijn | 523/114 |
| 4,131,597 | 12/1978 | Bluethgen et al. | 523/114 |
| 4,192,021 | 3/1980 | Deibig et al. | 523/116 |
| 4,373,217 | 2/1983 | Draenert | 523/115 |
| 4,500,658 | 2/1985 | Fox | 523/117 |
| 4,526,909 | 7/1985 | Urist | 523/115 |
| 4,547,390 | 10/1985 | Ashman et al. | 427/336 |
| 4,617,327 | 10/1986 | Podszun | 523/116 |
| 4,652,593 | 3/1987 | Kawalara et al. | 523/116 |
| 4,843,112 | 6/1989 | Germart et al. | 523/115 |
| 4,898,734 | 2/1990 | Mathiowitz et al. | 424/426 |
| 4,963,151 | 10/1990 | Ducheyne et al. | 623/16 |
| 5,271,961 | 12/1993 | Mathiowitz et al. | 427/213 |
| 5,276,070 | 1/1994 | Arroyo | 523/117 |
| 5,334,626 | 8/1994 | Lin | 523/116 |

FOREIGN PATENT DOCUMENTS

| | | |
|---|---|---|
| 0 041 614 | 12/1981 | European Pat. Off. . |
| 0 047 971 | 3/1982 | European Pat. Off. . |
| 2 344 280 | 10/1977 | France . |
| 29 05 878 | 8/1980 | Germany . |
| 4029136 | 9/1990 | Germany . |
| 4029714 | 9/1990 | Germany . |

OTHER PUBLICATIONS

"Chemical Dictionary" by Grant & Hackh's Fifth Edition, p. 294, 1987.

*Primary Examiner*—Andrew E. C. Merriam
*Attorney, Agent, or Firm*—Kinney & Lange, P.A.

[57] ABSTRACT

A multiple component material, in particular a filler particle containing implantation material is produced and used to anchor prothesis components in bones, to strengthen bones, as dowel for bone screws and as implants for anchoring screws. The polymer component of the disclosed implantation material is preferably based on an acrylate or polymethacrylate basis, or on an acrylate and methacrylate copolymer or a mixture thereof. The polymer component encloses the filler particles at least in part. Preferably, the filler particles are 5 to 15 μm in size and have at least 50% void volume. The multiple component material is stored in a dry, stable particulate form ready for use by mixing with monomer liquid.

20 Claims, 1 Drawing Sheet

MULTI-COMPONENT MATERIAL AND PROCESS FOR ITS PREPARATION

CROSS-REFERENCE TO RELATED APPLICATION(S)

This application is a continuation of application Ser. No. 08/650,047, filed May 16, 1996, now abandoned which was a continuation of application Ser. No. 08/030,045 filed May 2, 1994, now abandoned, which was a 371 National Phase Application of PCT/EP91/01746 filed Sep. 13, 1991.

BACKGROUND OF THE INVENTION

The invention relates to a multi-component material, in particular a two-component material with admixtures, for example in the form of filler particles. The invention relates in particular to an implant material which contains a polymer and/or copolymer as well as filler particles. Such implant materials are used to anchor prosthesis components in bone and to reinforce the bone and additionally as the dowel of bone screws or as implants for anchoring screws, for example in the case of composite osteosyntheses. In particular polymer acrylate and especially polymethyl acrylate are used as the polymer. The invention will be described in the following with such an implant material but it also comprises any multi-component material consisting of at least one polymer component and at least one monomeric component as well as admixtures, in particular particle-shaped admixtures.

The above implant materials are known as bone cements and have been clinically tested. They are not absorbed by the body but are biologically inert and are integrated into the osseous system. Known bone cements consist of a polymer component, which is generally in the form of spherules and is also referred to as a bead polymer, a monomeric component and optionally a polymerization catalyst, a stabilizer and an activator. Before they are used, the components are mixed as homogeneously as possible. Bone cements on an acrylate base have proven to be advantageous anchorage materials for prosthesis components. However, the disadvantage of such bone cements consists in the fact that despite improved mixing and application methods the material strength and reproducibility has not yet been able to be optimized reliably. The bone cements can wear in the course of their clinical use and show signs of increasing breakage, as a result of which bone absorption and the consequently inevitable displacement of the implant may arise.

As a rule, filler particles are added to the cited implant materials, in particularly to create a certain porosity which should lead to an improved bond between the implant and the bone as a result of the regrowth of osseous tissue.

It is known from DE-A-29 05 878 that one of the problems with bone cements comprising filler particles, so-called filler cements, consists in the fact that the pores of the filler particles absorb the monomer and that this monomer is thus no longer available for the embedding of the polymer powder. This can result in an incomplete polymerization and in the penetration of the monomer into the circulatory system of the patient. Furthermore, the pores cannot be designed in the desired manner and the strength of the bone cement can possibly be reduced. In DE-A-29 05 878 an attempt is made to solve this problem by temporarily closing the pore volume in order to prevent the penetration of monomers. However, the filler particles should be as freely accessible to the bone as possible and cannot be completely embedded into the bone cement since their free surface would otherwise be no longer accessible to the bone.

In addition to the cited filler particles which according to DE-A-29 05 878 preferably consist of absorbable tricalcium phosphate, radiographic contrast agents and antibiotics for example can also be understood as filler particles in the general sense. The term "filler particle" within the scope of the invention should thus also include, for example, radiographic contrast agents and antibiotics. It has already been shown (Lee A. J. C., Ling R. S. M., Vangala, S. S., Arch. Orthop. Traumat. Surg. 92, 1–18, 1978) that radiographic contrast agents and antibiotics also cause a clear decrease in the strength of the bone cement which can be between 4% and 25%. It has likewise also been demonstrated (Klaus Draenert, Forschung und Fortbildung in der Chirurgie des Bewegungsapparats 2, zur Praxis der Zementverankerung, Art und Science, München, page 39, 1988, ISDN 3-923112-11-4) that in particular the radiographic contrast agents show filling defects in the secondary polymerizing matrix of the bone cement.

In a normal packing of bone cement with 40 g polymer powder, up to 6 g radiographic contrast agent, usually in the form of barium sulfate or zirconium dioxide, is added. Bismuthic compounds can also be used. It is also known from DE-A-29 05 878 that hydroxylapatite can give a sufficient radiographic contrast of the bone cement implant if added in appropriate amounts. The radiographic contrast agents fulfill their function as an X-ray-impermeable material in contrast to the porous filler particles in the narrower sense, even if they are embedded in bone cement.

Apart from the decrease in the strength of the bone cement the addition of radiographic contrast agents of the filler also presents the problem that the admixture of this filler and in particular the reproducibility of the homogeneity of the mixture can lead to not inconsiderable problems with the industrial production of the polymer powder. It has been shown that, despite polished techniques with ball mills and various shakers, individual packings of bone cement frequently contain so-called conglomerates of radiographic contrast agents which cause the monomer to be absorbed with the result that the mixing conditions and the viscosity of this bone cement charge can differ completely from that of normal bone cements. It was also established that the radiographic contrast agents, for example the zirconium dioxide, of various producers can differ and that in particular barium sulfate tends to form the so-called conglomerates.

BRIEF SUMMARY OF THE INVENTION

The object of the invention is thus to overcome the above disadvantages and to provide a multi-component material comprising admixtures, in particular a two-component material, wherein the particle-shaped admixtures do not cause a decrease in the strength of the multi-component material, nor any filling defects.

In particular, it is the object of the invention to overcome the above disadvantages and to provide an implant material comprising filler particles, such as bone cement, wherein the filler particles do not cause a decrease in the strength of the implant material, nor any filling defects. A further object of the invention consists in distributing the filler particles homogeneously and reproducibly in the implant material. A further object of the invention is to provide a process for the preparation of a multi-component material containing admixtures, in particular particle-shaped admixtures, in particular of an implant material containing filler particles, having the above advantages.

This object is achieved by the multi-component material, in particular the implant material, and the process according to the invention. The invention is based on the idea of taking suitable measures so that the polymer component of the material, which ensures that the self-curing mixture of monomer and polymer can harden within the useful and desired period of time, can accommodate the admixtures, e.g. the filler particles, in an ideal manner. For this purpose, during the preparation of the material the filler particles or other admixtures are at least partially encompassed by the polymer particles, for example coated with the polymer particles or otherwise embedded in these. This enables the cited problems with the incorporation of the filler particles or other admixtures to be solved in a simple and elegant manner.

BRIEF DESCRIPTION OF THE DRAWING

The FIGURE shows the embodiment of Example 3, including a polymer sphere with a diameter of approximately 80 μm with embedded zirconium dioxide radiographic contrast agent particles in dark.

DETAILED DESCRIPTION

Figure 1:
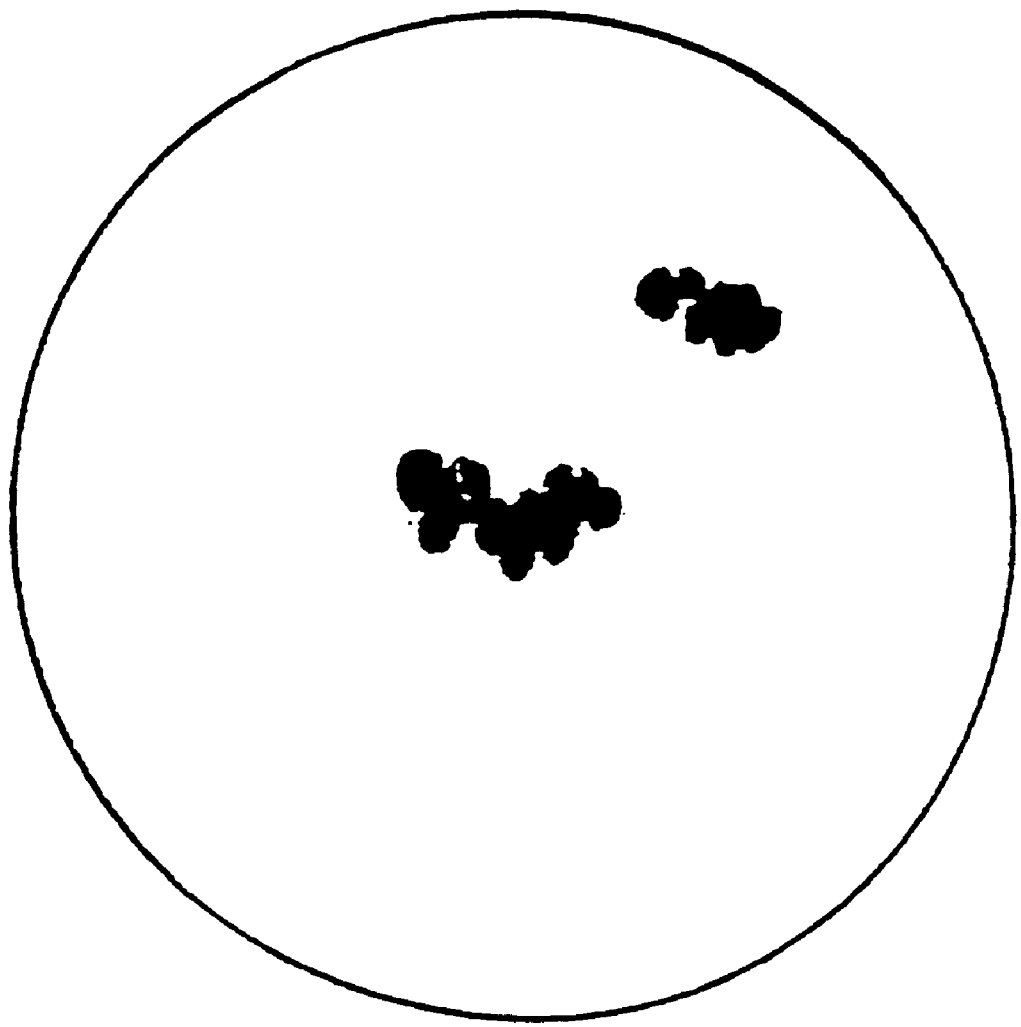

In the present description the term polymer is to be understood to also comprise copolymers. According to the invention, polymers on a polyacrylate or polymethacrylate base, copolymers of an acrylate and a methacrylate, mixtures of the cited polymers and copolymers, epoxy resin or a polymer of another plastic usable as an implant material are preferably used.

The filler particles, for example radiographic contrast agents, are preferably 5 to 15 μm in size. In contrast, the polymer spheres of the powder component are larger and have, for example for the conventional Palacos R®-cement, a size distribution between 1 and 140 μm with a maximum of sizes being between 60 and 80 μm. The particles are generally approximately spherical and the above size specifications refer in this case to the diameters of the spheres. Should the particles not be spherical, the average diameter of the particles is to be understood by the above size specifications. The filler particles can be up to 250 μm in size and the polymer particles can be up to 300 μm in size.

In the process according to the invention, the smaller filler particles, for example radiographic contrast agent particles, are embedded during the preparation of the polymer particles as the nucleus of crystallization and in this manner the entire 6 g radiographic contrast agent required for a normal packing of bone cement can be accommodated by the polymer component without additional filler particles having to be added freely to the polymer powder. Thus, an additional porosity which would be capable of accommodating the monomer fluid can be prevented. Furthermore, wetting defects and gaps can be prevented from occurring on the interface between the radiographic contrast agent and the monomer. In addition, it is guaranteed that the radiographic contrast agent is incorporated in the far more stable polymer of the powder component and not in the less resistant matrix of the added monomer during final polymerization.

The embedding of the particles, e.g. of the radiographic contrast agent into the polymer does not cause the radiographic contrast agent to be prevented from fulfilling its function as an X-ray impermeable material. $CrO_2$, $BaSO_4$, $Bi_2O_3$, $Bi(OH)_3$ and/or liquid or solid iodiferous contrast agents are preferably used as the radiographic contrast agents.

The filler particles can also contain active substances. It has namely been shown that active substances, for example antibiotics, are released by diffusion even if they are initially embedded into the polymer particles or coated by these. Therefore, according to the invention at least most of such substances, for example antibiotics, can also be accommodated by the polymer powder component. Gentamicin and/or clindamicin are preferably used as antibiotics.

Other active substances, too, which are gradually released from the polymer by diffusion, can be embedded into the polymer as filling material.

As embeddable filler particles hydroxylapatite, tricalcium phosphate or another calcium phosphate or calcium carbonate compound, an aluminum or aluminum oxide compound and/or a silicon compound can, for example, be embedded into the polymer particles or coated with these. Combinations of the cited filler particles are also possible.

According to DE-A-29 05 878 the pore volume of the tricalcium phosphate filler particles is preferably less than 0.1 ml/g. In the implant material according to the invention, the filler particles can have a high porosity since they are embedded into the polymer or coated by this. The filler particles can preferably have a porosity of 20 to 80%. Filler particles with a porosity of at least 50% can also be used. On the other hand, it is also possible to incorporate dense filler particles with a pore volume of virtually 0, which merely have a microporosity, into the implant material according to the invention.

In order to prepare the implant material according to the invention all processes are suitable with which the filler particles can be at least partially coated with the polymer or embedded in this. Various known and common processes are suitable for this. For example, the coating can be effected by the polymer being formed together with the filler particles in a precipitation solution in a spraying process. The coating or embedding of the filler particles into the polymer can also be effected by precipitation, electrostatic coating, coating by a dipping process or coating by a pelleting process or by other known processes.

The inclusion of fillers, for example radiographic contrast agent particles, can be achieved in a particularly simple and preferable manner by melting a conventional bone cement, preferably in the form of bead polymers, with fillers homogeneously mixed therewith, for example zirconium dioxide radiographic contrast agent particles and subsequently pressing it out under high pressure through a suitable nozzle into a precipitation bath, for example by means of an injection moulding machine. As a rule pressures of approximately 300 bar are applied but the pressure can also be up to 2000 bar. The smaller the precipitated particles should be, the finer the nozzle and the higher the pressure applied should be. With conventional bone cements, such as Palacos R®-cement, the temperature is approximately 190 to 255° C. since the polymer burns at temperatures slightly above 250° C. The irregular surface of the fillers 5 to 15 μm in size offers a large adhesive surface which provides a reliable inclusion of the fillers into the polymer component. In the precipitation bath, too, the polymer adheres to the filler particles for the longest period of time so that all filler particles remain incorporated. This method of preparation is inexpensive and moreover offers the advantage that starting materials which have already been clinically tested can be used for the preparation of the implant material.

It is also possible to prepare the polymer material as a compact block of any form and to then crush it to granules of a suitable particle size. In this way, no polymer spheres are formed but rather irregularly formed particles. It has been shown that bone cements with clearly improved mechanical properties are obtained if a polymer component obtained in this manner is used. It is not necessary for the entire polymer component to consist of such granules; rather it should be at least 1 to 50 weight percent, whilst very good results can already be obtained with 5 to 20 weight percent.

If the filler particles are introduced into this polymer block, e.g. by working them into the molten mass or by mixing them into the monomer fluid and subsequent polymerization, granular particles both with and without enclosed filler particles are obtained during crushing. It is possible to use such granules directly. Alternatively, granulates without filler particles can also be used together with polymer coated filler particles obtained in a different manner.

The use of irregular granules obtained from a polymer block by crushing or pulverization is also very advantageous independent of the use of the polymer coated filler particles of the present application. Even with normal bone cements, in which free filler particles are present, a better mechanical stability is achieved by replacing the spherical prepolymer by at least 1 to 50 weight percent of granules.

The implant materials according to the present invention are excellent for anchoring prosthesis components in bone and for reinforcing bone. Furthermore, the implant material according to the present invention can also be used as a dowel of bone screws or as an implant for anchoring screws, for example in the case of composite osteosyntheses.

An advantage of the implant material of the invention consists in the fact that the mixing behaviour is not negatively influenced when the implant material is being used, for example as bone cement, whereby the reproducibility of homogeneous charges can be improved considerably. A further advantage consists in the fact that a considerably more uniform active substance release from the implant material in considerably higher concentrations can take place. Finally, it is also an advantage that the lower monomer consumption reduces the temperature during the curing of the implant,material and increases the mechanical stability of the material drastically, and the radiographic contrast is distributed much more uniformly.

EXAMPLE 1

1000 g of polymethylmethacrylate granules are melted together with 150 g zirconium dioxide serving as a radiographic contrast agent and the molten mass is subsequently pressed out through a nozzle in a precipitation bath. Polymer spheres are formed in which the zirconium dioxide is embedded. The resultant polymer spheres are subsequently sieved through various sieves and dried and finally collected within a range of 1 and 140 $\mu$m, filled into a container, treated with benzylperoxide and then packed ready for use.

EXAMPLE 2

1000 g of polymethylmethacrylate granules are liquefied by heat and separately pressed out with 150 g zirconium dioxide into a precipitation bath in a spraying unit. In this process, the zirconium dioxide particles are coated with polymethylmethacrylate and the polymethylmethacrylate spheres containing the zirconium dioxide collect in the precipitation bath and are filtered in the manner described in Example 1 and packed, with benzylperoxide being added.

EXAMPLE 3

1000 g of a conventional polymethylmethacrylate bead polymer are blended homogeneously together with 150 g zirconium dioxide serving as a radiographic contrast agent and then heated in a chamber to 250° C. and thereby liquefied. The molten mass is subsequently extruded with pressures of approximately 300 bar through a nozzle into a precipitation bath. Polymer spheres are formed in which the zirconium dioxide is embedded. The resultant polymer spheres are subsequently sieved through various sieves and dried and finally collected in a range of 1 and 140 $\mu$m, filled into a container, treated with benzylperoxide and packed ready for use. A polymer sphere with a diameter of approximately 80 $\mu$m is shown in the Figure with the embedded zirconium dioxide radiographic contrast agent particles in dark.

What is claimed is:

1. A polymerizable bone cement constituent material stored in dry, stable particulate form which is ready for use by mixing with monomer liquid to induce final polymerization into a bone cement implantation material, the bone cement constituent material comprising:
   a prepolymerization component consisting of particles selected from the group consisting of an acrylate polymer, a methacrylate polymer, a methylmethacrylate polymer, and copolymers thereof, and
   a filler component consisting of filler particles comprising at least one active substance;
   wherein the bone cement constituent material is stored in dry, stable particulate form of particles no greater than 300 $\mu$m in size and having at least some of the filler particles at least partially embedded into individual particles of the prepolymerization component before the prepolymerization component reacts with the monomer liquid for final polymerization, said prepolymerization component being polymerizable by mixing the bone cement constituent material with monomer liquid into a bone cement implantation material which is biologically inert, said filler particles being accessible in the individual particles of the prepolymerization component for release from the bone cement implantation material by diffusion.

2. The bone cement constituent material according to claim 1, wherein at least some of the filler particles are completely embedded into individual particles of the prepolymerization component before the prepolymerization component reacts with monomer liquid for final polymerization, and the completely embedded filler particles are accessible for release by diffusion each through the individual particle of the prepolymerization component in which said filler particle is embedded.

3. The bone cement constituent material according to claim 1, wherein said filler particles are only partially embedded into individual polymer and/or copolymer particles.

4. The bone cement constituent material according to claim 1, wherein the filler particles are 1 to 250 $\mu$m in size.

5. The bone cement constituent material according to claim 4, wherein the filler particles are 5 to 15 $\mu$m in size.

6. The bone cement constituent material according to claim 1, wherein the active substance is an antibiotic.

7. A polymerizable bone cement constituent material stored in dry, stable powder form which is ready for use by mixing with monomer liquid to induce final polymerization into a bone cement implantation material, the bone cement constituent material comprising:
   a prepolymerization component consisting of particles selected from the group consisting of an acrylate polymer, a methacrylate polymer, a methylmethacrylate polymer, and copolymers thereof; and
   a filler component consisting of filler particles comprising hydroxylapatite, tricalcium phosphate and/or another calcium phosphate or calcium carbonate compound, an aluminum or an aluminum oxide compound and/or a silicon compound;

wherein the bone cement constituent material is stored in dry, stable powder form having individual filler particles only partially embedded into individual polymer and/or copolymer particles before the prepolymerization component reacts with the monomer liquid for final polymerization, said prepolymerization component being polymerizable by mixing the bone cement constituent material with monomer liquid into a bone cement implantation material which is biologically inert, said partially embedded filler particles providing a free surface extending from the individual polymer and/or copolymer particles, said free surface being accessible to bone after final polymerization and upon implantation.

8. The bone cement constituent material according to claim 7 wherein the filler particles have a porosity of 20 to 80%.

9. A material in particle form for subsequent use by combining with a liquid monomer to form a bone cement material, the material consisting essentially of:

50 to 99% by weight of polymer beads based on a plastics material selected from the group consisting of acrylate, methacrylate, methylmethacrylate, epoxy resin and copolymers thereof; and 1 to 50% by weight of irregularly shaped granules comprising polymer particles, the polymer particles based on a plastics material selected from the group consisting of acrylate, methacrylate, methylmethacrylate, epoxy resin and copolymers thereof.

10. The material of claim 9, consisting essentially of 80 to 95% by weight of the polymer beads and 5 to 25% by weight of the irregularly shaped granules.

11. A polymerizable bone cement constituent material stored in dry, stable particulate form which is ready for use by mixing with monomer liquid to induce final polymerization into a bone cement implantation material, the bone cement constituent material comprising a prepolymerization component and a filler component, said prepolymerization component consisting of particles selected from the group consisting of an acrylate polymer, a methacrylate polymer, a methylmethacrylate polymer, and copolymers thereof, said filler component consisting of filler particles of a material different from the material of the polymer and/or copolymer particles, wherein the bone cement constituent material is stored in dry, stable particulate form having at least some of the filler particles at least partially embedded into individual polymer and/or copolymer particles before the prepolymerization component is finally polymerized, and wherein the bone cement constituent material is in a crushed form having irregularly shaped granules.

12. A polymerizable bone cement constituent material stored in dry, stable particulate form which is ready for use by mixing with monomer liquid to induce final polymerization into a bone cement implantation material, the bone cement constituent material comprising:

a prepolymerization component consisting of particles selected from the group consisting of an acrylate polymer, a methacrylate polymer, a methylmethacrylate polymer, and copolymers thereof, and a filler component consisting of filler particles of a radiographic contrast agent;

wherein the bone cement constituent material is stored in dry, stable powder form having individual filler particles at least partially embedded into individual polymer and/or copolymer particles before the prepolymerization component reacts with the monomer liquid for final polymerization, said prepolymerization component being polymerizable by mixing the bone cement constituent material with monomer liquid into a bone cement implantation material which is biologically inert.

13. The bone cement constituent material of claim 1, wherein the bone cement constituent material consists essentially of the filler particles and the individual polymer and/or copolymer particles, such that the filler particles directly contact the individual polymer and/or copolymer particles.

14. The bone cement constituent material of claim 7, wherein the bone cement constituent particles are no greater than 300 $\mu$m in size.

15. The bone cement constituent material of claim 7, wherein the bone cement constituent material consists essentially of the filler particles and the individual polymer and/or copolymer particles, such that the filler particles directly contact the individual polymer and/or copolymer particles.

16. The bone cement constituent material of claim 9, wherein the bone cement constituent particles are no greater than 300 $\mu$m in size.

17. The bone cement constituent material of claim 11, wherein the bone cement constituent particles are no greater than 300 $\mu$m in size.

18. The bone cement constituent material of claim 11, wherein the bone cement constituent material consists essentially of the filler particles and the individual polymer and/or copolymer particles, such that the filler particles directly contact the individual polymer and/or copolymer particles.

19. The bone cement constituent material of claim 12, wherein the bone cement constituent particles are no greater than 300 $\mu$m in size.

20. The bone cement constituent material of claim 12, packed with benzylperoxide.

* * * * *